United States Patent
Yamazaki et al.

(10) Patent No.: US 10,066,931 B2
(45) Date of Patent: Sep. 4, 2018

(54) OPTICAL INNER-SURFACE MEASUREMENT DEVICE

(71) Applicant: Adamant Namiki Precision Jewel Co., Ltd., Tokyo (JP)

(72) Inventors: Hiroshi Yamazaki, Kuroishi (JP); Eri Fukushima, Kuroishi (JP); Kazumi Yanagiura, Kuroishi (JP); Takafumi Asada, Kuroishi (JP)

(73) Assignee: Adamant Namiki Precision Jewel Co., Ltd., Tokyo (JP)

( * ) Notice: Subject to any disclaimer, the term of this patent is extended or adjusted under 35 U.S.C. 154(b) by 0 days.

(21) Appl. No.: 15/597,358

(22) Filed: May 17, 2017

(65) Prior Publication Data

US 2017/0248411 A1    Aug. 31, 2017

Related U.S. Application Data

(63) Continuation of application No. PCT/JP2015/082088, filed on Nov. 16, 2015.

(30) Foreign Application Priority Data

Nov. 25, 2014    (JP) ................ 2014-238107

(51) Int. Cl.
*G01B 9/02* (2006.01)
*G01B 11/24* (2006.01)
*G01B 11/12* (2006.01)

(52) U.S. Cl.
CPC .......... *G01B 11/2441* (2013.01); *G01B 11/12* (2013.01)

(58) Field of Classification Search
CPC .. G01B 9/02049; G01B 9/0205; G01B 11/12; G01B 11/2441
See application file for complete search history.

(56) References Cited

U.S. PATENT DOCUMENTS

| | | | |
|---|---|---|---|
| 5,325,177 A | 6/1994 | Peterson | |
| 2008/0259346 A1* | 10/2008 | Strahle | G01B 11/12 356/496 |
| 2014/0275986 A1* | 9/2014 | Vertikov | A61B 5/061 600/424 |

FOREIGN PATENT DOCUMENTS

| | | |
|---|---|---|
| JP | H05-180627 A | 7/1993 |
| JP | H08-233545 A | 9/1996 |
| JP | H11-281331 A | 10/1999 |
| JP | 2009-236614 A | 10/2009 |
| JP | 2010-236870 A | 10/2010 |

(Continued)

OTHER PUBLICATIONS

International Search Report issued in PCT/JP2015/082088; dated Dec. 8, 2015.

*Primary Examiner* — Jonathan Hansen
(74) *Attorney, Agent, or Firm* — Studebaker & Brackett PC

(57) ABSTRACT

An optical inner-surface measurement device includes: an optical fiber included inside a tube, the optical fiber being configured to be inserted into a hole of an inspection object; at least two optical-path converting elements disposed in a forward-end of the optical fiber; and a motor for rotationally driving at least one of the at least two optical-path converting elements. The at least two optical-path converting elements emit a light beam, guided thereto through the optical fiber, to an inner peripheral surface of the hole of the inspection object three-dimensionally in a circumferential direction and an axial direction of the hole.

8 Claims, 15 Drawing Sheets

(56) References Cited

FOREIGN PATENT DOCUMENTS

WO        2014/054666   A1     4/2014
WO        2015/022760   A1     2/2015

\* cited by examiner

100a

OPTICAL INNER-SURFACE MEASUREMENT DEVICE

CROSS-REFERENCE TO RELATED APPLICATION

The present application is a continuation application of International Application No. PCT/JP2015/082088, filed on Nov. 16, 2015, which claims priority to Japanese Patent Application No. 2014-238107, on Nov. 25, 2014. The contents of these applications are incorporated herein by reference in their entirety.

BACKGROUND

1. Technical Field

The present disclosure relates to an optical inner-surface measurement device.

2. Description of the Related Art

Power performance and a fuel consumption efficiency of an automobile are largely affected by, e.g., qualities of a finished dimension and a geometric accuracy of a cylinder of an automobile engine. These qualities are generally inspected by use of a contact-type measuring device such as a roundness measuring instrument, a surface roughness tester, and a length measuring machine including a linear scale. Recently, however, in order to perform the inspection without damaging a measurement object (an object to be measured), an optical non-contact-type measuring device has been proposed.

One example of a technique for observing and inspecting the presence or absence of a damage on an inner surface of a measurement object in a non-contact manner is a diagnostic imaging technique (optical imaging technique). This technique is widely used for purposes such as inspection of various mechanical parts, devices, and equipment in sites such as a medical site. For example, in a manufacturing site for, e.g., precision equipment, the inspection and the diagnostic imaging with respect to a deepest part of a deep hole may be performed by camera observation with a general endoscope. Alternatively to the camera observation, an automatic inspection as below may be employed. That is, according to the automatic inspection, an inspection object (an object to be inspected) is irradiated with a light beam, strength of reflected light is detected by an optical sensor, and determination by a computer is executed.

Meanwhile, in a medical field, various techniques are researched and used to observe a diseased part inside a human body. The various techniques encompass X-ray computed tomography, nuclear magnetic resonance, and OCT imaging (optical coherence tomography) by an endoscope, which makes use of optical coherency. Each of these techniques enables observation of a tomographic image.

In some cases, the above measurement device may employ near-infrared light, which is used as a light source in the medical field. In this arrangement, in a case where the measurement object has a deep hole having an inner peripheral surface made from metal, near-infrared light is reflected by the inner peripheral surface. Meanwhile, in a case where the inner peripheral surface made from metal includes a resin-film layer formed thereon, near-infrared light is semi-transmitted through the resin. Thus, simultaneously with observation of a three-dimensional shape of the inner peripheral surface, it is possible to perform measurement of a thickness accuracy of the resin film and observation of a pinhole on the resin surface.

For example, JP-A-08-233545, JP-A-05-180627, and JP-A-2010-236870 disclose representative structures of an observation device employing the technique for observing or measuring an inner peripheral surface of a mechanical part by irradiating the inner peripheral surface with a light beam.

FIGS. 1 to 4 each show an optical probe of a known optical inner-surface measurement device. In a probe 11 shown in FIGS. 1 to 4, a rotational optical fiber 1 is supported by bearings 5a and 5b inside a tube 3. Inside a probe case 6, the rotational optical fiber 1 is rotated by a fiber-rotating motor 10, pulleys 7 and 8, and a belt 9. Consequently, a mirror 2 with a hemispherical lens is rotated. The mirror 2 with the hemispherical lens is attached to a forward-end of the rotational optical fiber 1. A light beam is guided through the rotational optical fiber 1, and is emitted from the mirror 2 with the hemispherical lens. The light beam is then transmitted through a light-transmitting member, and is emitted to an inspection object 100a. A reflected light from the inspection object 100a is guided to the rotational optical fiber 1 again. In this manner, a roundness is measured.

In a state shown in FIG. 1, a hole of the inspection object 100a is favorably set at a right angle with respect to a light beam to be emitted, rather than at an inclined angle. Consequently, d1 and d2 shown in FIG. 2 are measured correctly, and thus a roundness is also indicated correctly.

Meanwhile, in a state shown in FIG. 3, a hole of an inspection object 100b is set at an inclined angle with respect to a light beam to be emitted. Consequently, as shown in FIG. 4, a measured length dx is longer than an actual length, and thus a roundness cannot be measured correctly, either.

SUMMARY

An optical inner-surface measurement device includes: an optical fiber included inside a tube, the optical fiber being configured to be inserted into a hole of an inspection object; at least two optical-path converting elements disposed in a forward-end of the optical fiber; and a motor for rotationally driving at least one of the at least two optical-path converting elements. The at least two optical-path converting elements emit a light beam, guided thereto through the optical fiber, to an inner peripheral surface of the hole of the inspection object three-dimensionally in a circumferential direction and an axial direction of the hole.

DESCRIPTION OF THE EMBODIMENTS

Figure 1:
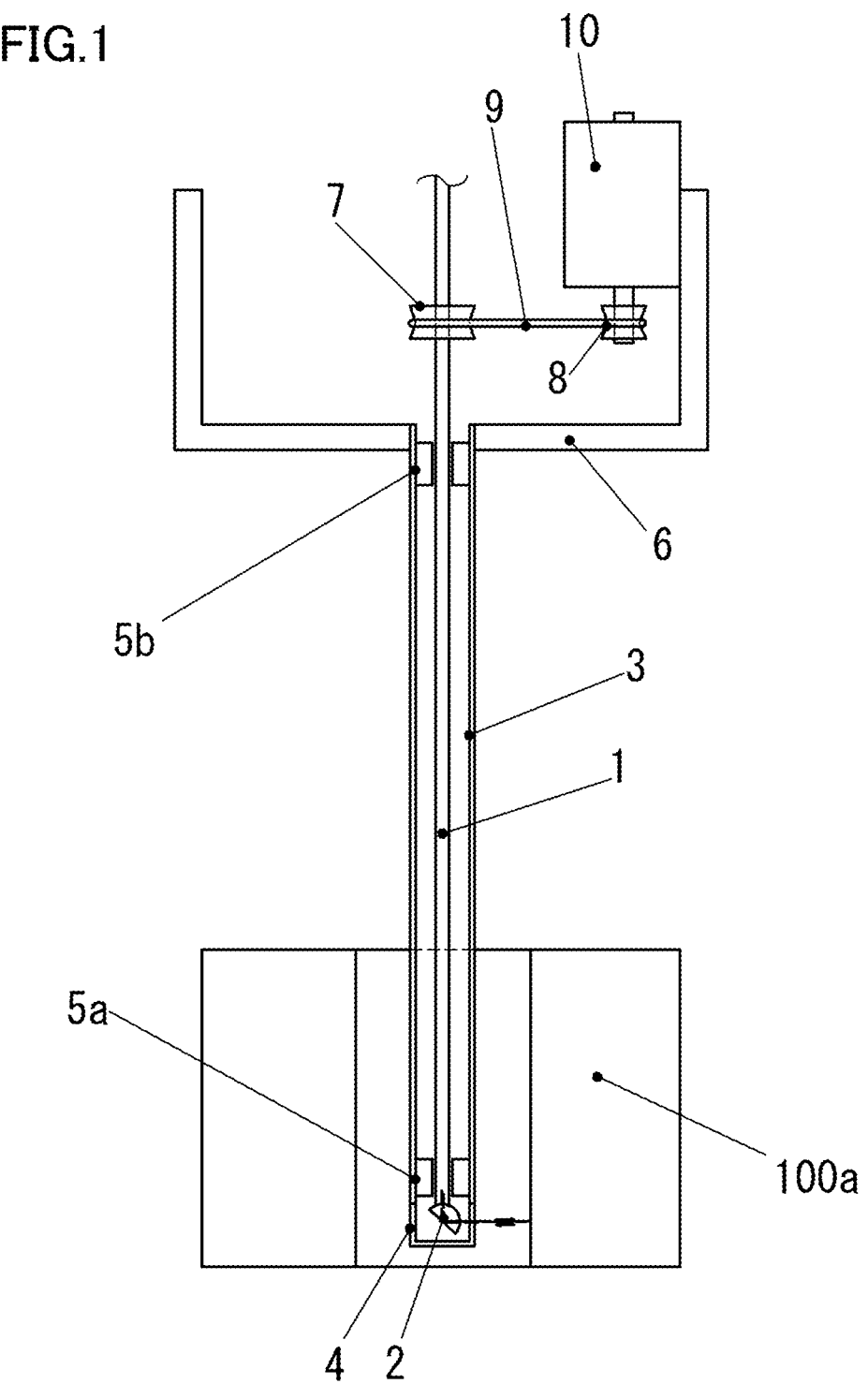
FIG. 1 illustrates a configuration of a known optical inner-surface measurement device.
Figure 2:
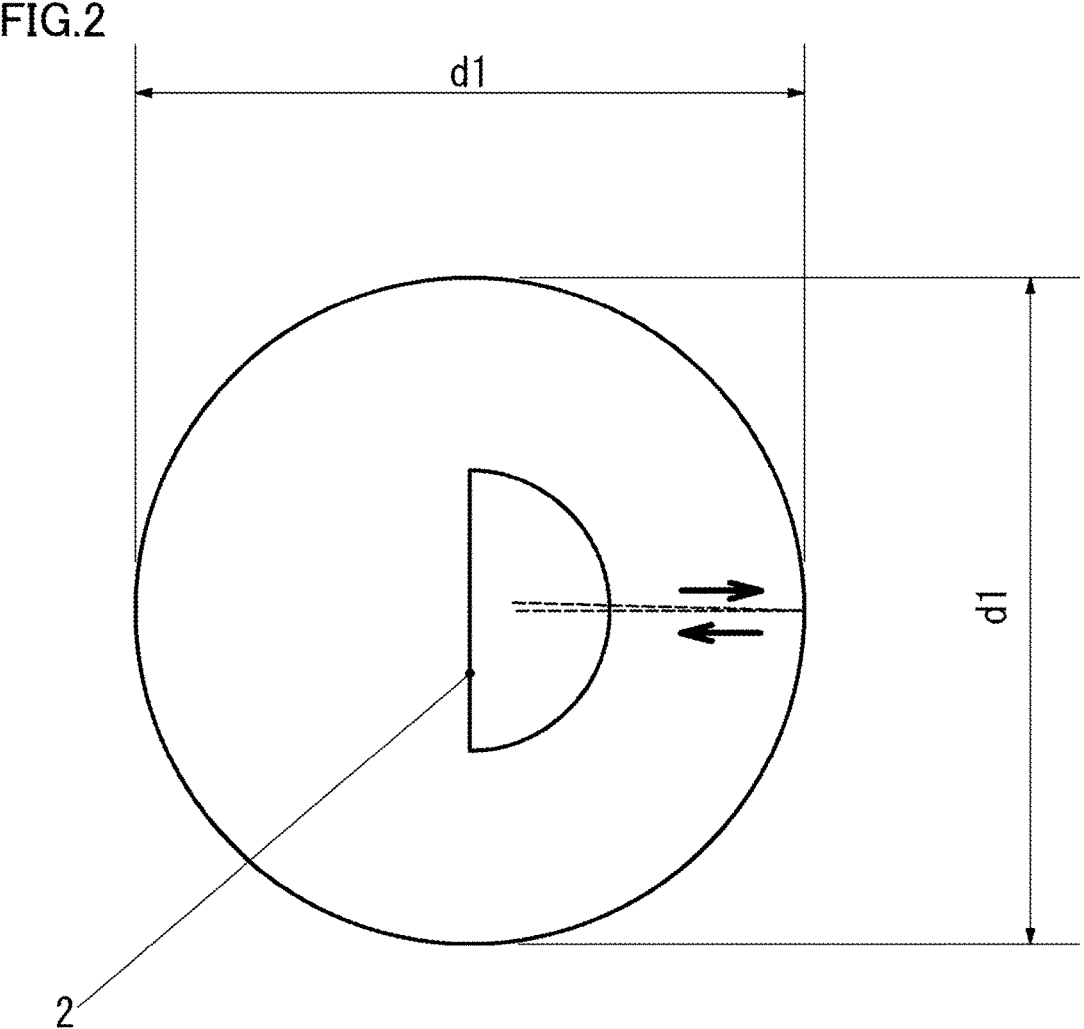
FIG. 2 is a cross-sectional view of an optical probe of the optical inner-surface measurement device.
Figure 3:
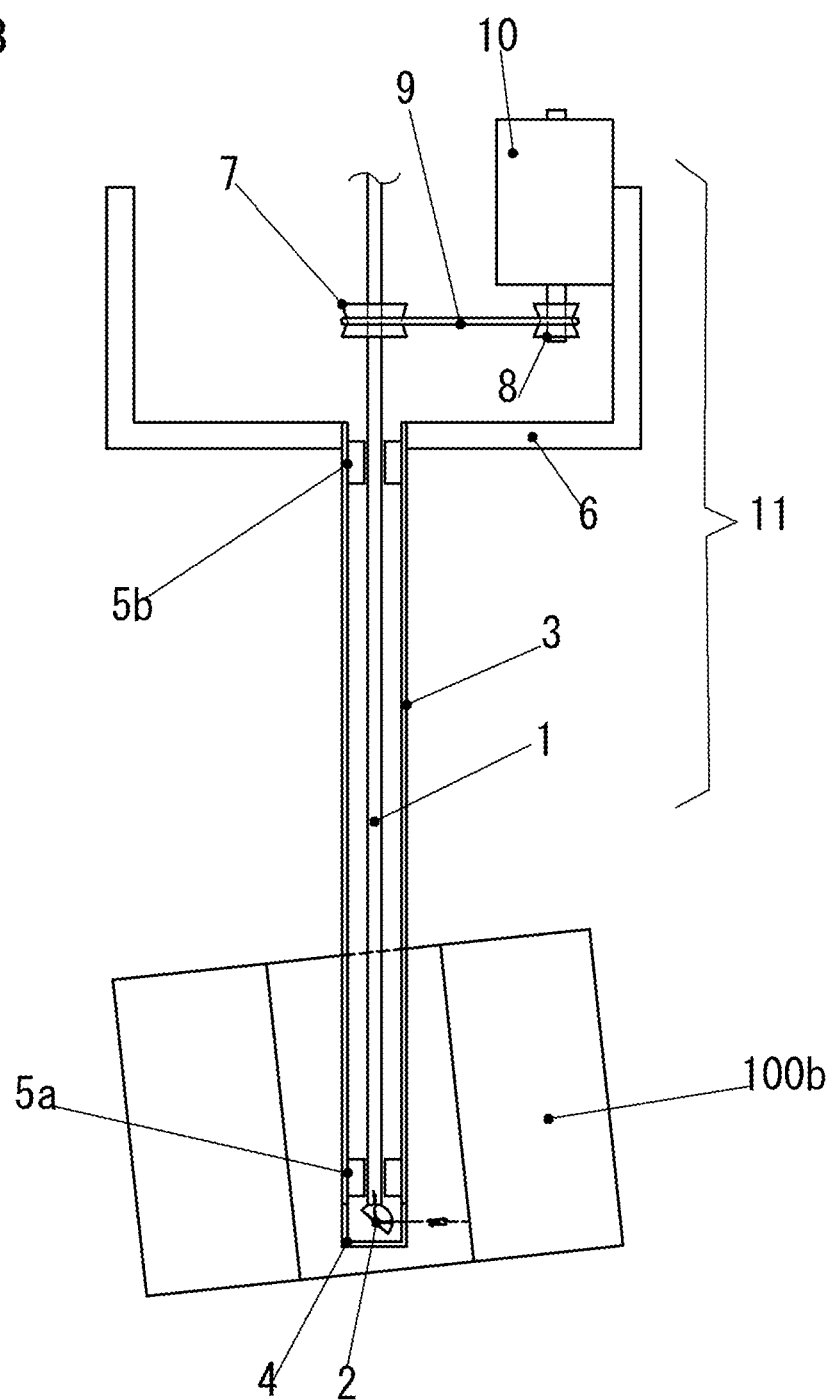
FIG. 3 is an explanatory view illustrating a state where a measurement object is inclined with respect to the optical inner-surface measurement device.
Figure 4:
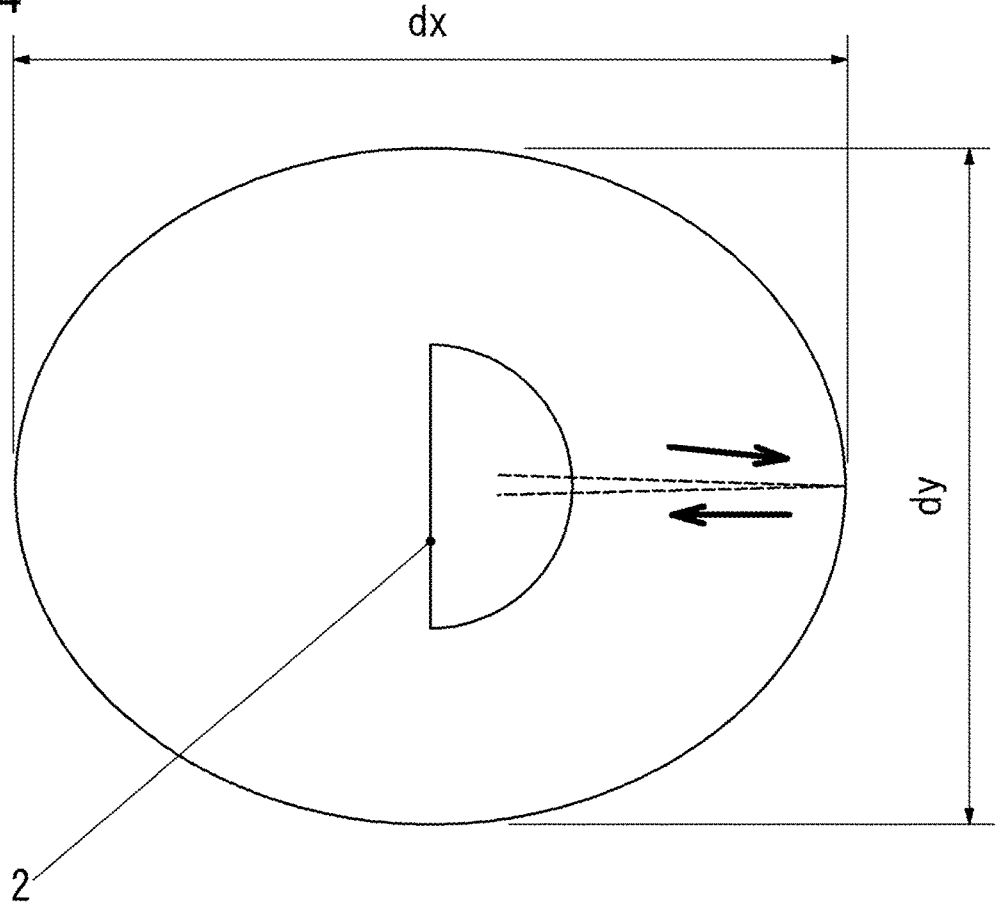
FIG. 4 is a cross-sectional view of the optical probe in the state shown in FIG. 3.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

One object of the present disclosure is to provide an optical inner-surface measurement device as below. In the optical inner-surface measurement device, a measuring probe is advanced to an inner peripheral surface of a measurement object, into an inner diameter of a deep hole of the measurement object, or into an inner circumference of a pipe that is long and bendable. Furthermore, a light beam is rotationally emitted to the inner peripheral surface or a bottom surface of the deep hole. The reflected light beam is collected three-dimensionally, and subjected to computer processing. Thus, the optical inner-surface measurement device is able to observe three-dimensional image data and to measure a dimension and a geometric accuracy.

Furthermore, the optical inner-surface measurement device is configured to eliminate the need for matching degrees of parallelization of the measuring probe and the measurement object and for performing alignment of the measuring probe and the measurement object, and thus is a measurement device that does not need to perform such troublesome settings. Moreover, the optical inner-surface measurement device is able to yield a measurement value that is less affected by a vibration caused by an advancing mechanism for causing the measuring probe to slide in its axial direction, and run out of a rotational shaft and a mechanical vibration that are caused by the rotational emission of the light beam to the inner peripheral surface that is to be measured. This suppresses or prevents a distortion and a vibration noise in image data, which are caused by the run out and the mechanical vibration according to a known technique. Thus, the optical inner-surface measurement device is able to correctly and accurately measure accuracies of the inner diameter and the inner peripheral surface.

An optical inner-surface measurement device according to an example of the present disclosure is configured to observe an inner peripheral surface of an inspection object and to measure an accuracy of a dimension of the inner peripheral surface, for example, by means of an interference optical technique (e.g., optical interferometry, a spectroscopic interference technique). This measurement device may include: an optical fiber included inside an optical measurement probe that is tubular, the optical fiber being configured to be inserted into a hole of an inspection object; at least two optical-path converting elements disposed in a forward-end of the optical fiber; and a motor for rotating at least one of these optical-path converting elements. For example, in a state where the tube is not being advanced in its axial direction but is stationary, the optical-path converting element is rotated so as to emit a light beam three-dimensionally in a circumferential direction and an axial direction of the hole.

This measurement device may further include a displacement detector for measuring an amount of run out of a rotational shaft of the motor. In this arrangement, for example, an optical interference analyzer calculates original waveform data regarding data indicative of a shape of an inner peripheral surface of the inspection object, based on reflected light guided thereto from the inner peripheral surface of the inspection object through the optical fiber. Furthermore, based on, e.g., data indicative of an angle of inclination of the inspection object and data indicative of an amount of displacement detected by the run out detector, the computer corrects the original waveform data and displays the original waveform data thus corrected.

This measurement device is configured to eliminate the need for matching degrees of parallelization of the measuring probe and the measurement object and for performing alignment of the measuring probe and the measurement object, and thus is a measurement device that does not need to perform such troublesome settings. Furthermore, with this measurement device, it is possible to suppress or prevent a distortion and a vibration noise in image data, which are caused by, e.g., a mechanical vibration according to a known technique. Thus, this measurement device is able to correctly and accurately measure accuracies of the inner diameter and the inner peripheral surface.

An optical inner-surface measurement device according to an aspect of the present disclosure (the present measurement device) includes: an optical fiber included inside a tube, the optical fiber being configured to be inserted into a hole of an inspection object; at least two optical-path converting elements disposed in a forward-end of the optical fiber; and a motor for rotationally driving at least one of the at least two optical-path converting elements. The at least two optical-path converting elements emit a light beam, guided thereto through the optical fiber, to an inner peripheral surface of the hole of the inspection object three-dimensionally in a circumferential direction and an axial direction of the hole.

According to the present measurement device, for example, an optical interference analyzer may calculate original waveform data regarding data indicative of a shape of the inner peripheral surface of the inspection object, based on reflected light guided thereto from the inner peripheral surface of the inspection object through the optical fiber. According to the present measurement device, for example, it is possible to collect three-dimensional data in a state where the optical fiber is not moving in the axial direction but is stationary. This makes it possible to measure the inner peripheral surface with a high accuracy.

The present measurement device may further include: an optical interference analyzer for receiving reflected light via the optical fiber and generating original waveform data regarding the inner peripheral surface, the reflected light being obtained by the light beam emitted three-dimensionally being reflected by the inner peripheral surface; and a computer for correcting the original waveform data.

The computer may calculate an angle of inclination of the inspection object, and correct the original waveform data based on a result of the calculation of the angle of the inclination.

The computer may calculate a roundness of the inner peripheral surface by correcting the original waveform data.

With the above arrangement, even in a case where the inspection object is inclined, the computer corrects the original waveform data according to an angle of the inclination. This makes it possible to measure a roundness correctly. This improves flexibility in setting a position of the inspection object. Consequently, it is possible even for an unskilled operator to easily perform the measurement with a high accuracy.

The present measurement device may further include a displacement detector for measuring an amount of rotational run out of at least one of the at least two optical-path converting elements that is rotating, and the computer may correct the original waveform data based on the amount of rotational run out.

With the above arrangement, the displacement detector collects the data indicative of the amount of rotational run out, and the computer corrects the original waveform data. This makes it possible to correctly measure accuracies of the inner diameter and the inner peripheral surface.

The displacement detector may include at least one sensor facing an outer peripheral surface of at least one of the at least two optical-path converting elements that is rotating.

With the above arrangement, the sensor collects the data indicative of the amount of rotational run out, and the computer corrects the original waveform data. This makes it possible to more correctly measure accuracies of the inner diameter and the inner peripheral surface.

The computer may generate data indicative of a shape of the inner peripheral surface of the inspection object by correcting the original waveform data based on the amount of rotational run out.

With the above arrangement, it is possible to remove, from the original waveform data, a distortion and a vibration in an image caused by the rotational run out and the vibration. This makes it possible to more correctly and accurately measure accuracies of the inner diameter and the inner peripheral surface.

The displacement detector may be configured to detect, as the amount of rotational run out, a difference between reference data of a shape of an inner peripheral surface or an outer peripheral surface of the tube or a light-transmitting member provided integrally with the tube and original waveform data regarding the inner peripheral surface or the outer peripheral surface, the original waveform data being obtained while the motor is rotating.

With the above arrangement, even without the run out sensor, it is possible to remove, from waveform data collected via the optical fiber, a distortion and a vibration in an image included in the data indicative of the shape of the inner peripheral surface of the inspection object. This makes it possible to correctly and accurately measure accuracies of the inner diameter and the inner peripheral surface.

The optical fiber may include a rotation-side optical fiber. The motor may include a first motor being disposed in a forward-end of the rotation-side optical fiber and including a rotational shaft that is hollow. The at least two optical-path converting elements may include a first optical-path converting element, the optical-path converting element being provided in a forward-end of the rotational shaft such that the first optical-path converting element is rotatable integrally with the rotational shaft. At least part of the forward-end of the rotation-side optical fiber may be inserted into a hollow hole of the rotational shaft such that the at least part of the forward-end of the rotation-side optical fiber is rotatable relative to the rotational shaft.

With the above arrangement, a rotational drive source (first motor) is disposed in the vicinity of the optical-path converting element. This reduces the amount of rotational run out, especially, non-repeatable run out. This reduces a distortion and a vibration in an image that are caused by the rotational run out and are given to the data indicative of the shape. This makes it possible to more accurately measure accuracies of the inner diameter and the inner peripheral surface.

The motor may further include a second motor disposed behind the first motor. The optical fiber may include a stationary-side optical fiber disposed behind the second motor and optically connected to the rotation-side optical fiber via a fixture. The second motor may include a rotational shaft that is hollow. At least part of a rear portion of the rotation-side optical fiber may be fixed to a hollow hole of the rotational shaft of the second motor. The at least two optical-path converting elements may include a second optical-path converting element attached to the forward-end of the rotation-side optical fiber.

With the above arrangement, electric wires for the first and second motors are not necessary to be located within a range scanned by the light beam emitted three-dimensionally. Thus, a shadow is hardly made in the light beam. This makes it possible to perform a highly-accurate measurement with data collected without missing.

Next, with reference to the drawings, the following describes preferred embodiments of the present disclosure.

An optical inner-surface measurement device (the present optical inner-surface measurement device) according to an embodiment of the present disclosure will be explained.

FIGS. 5 to 16 each show the present optical inner-surface measurement device.

Figure 5:
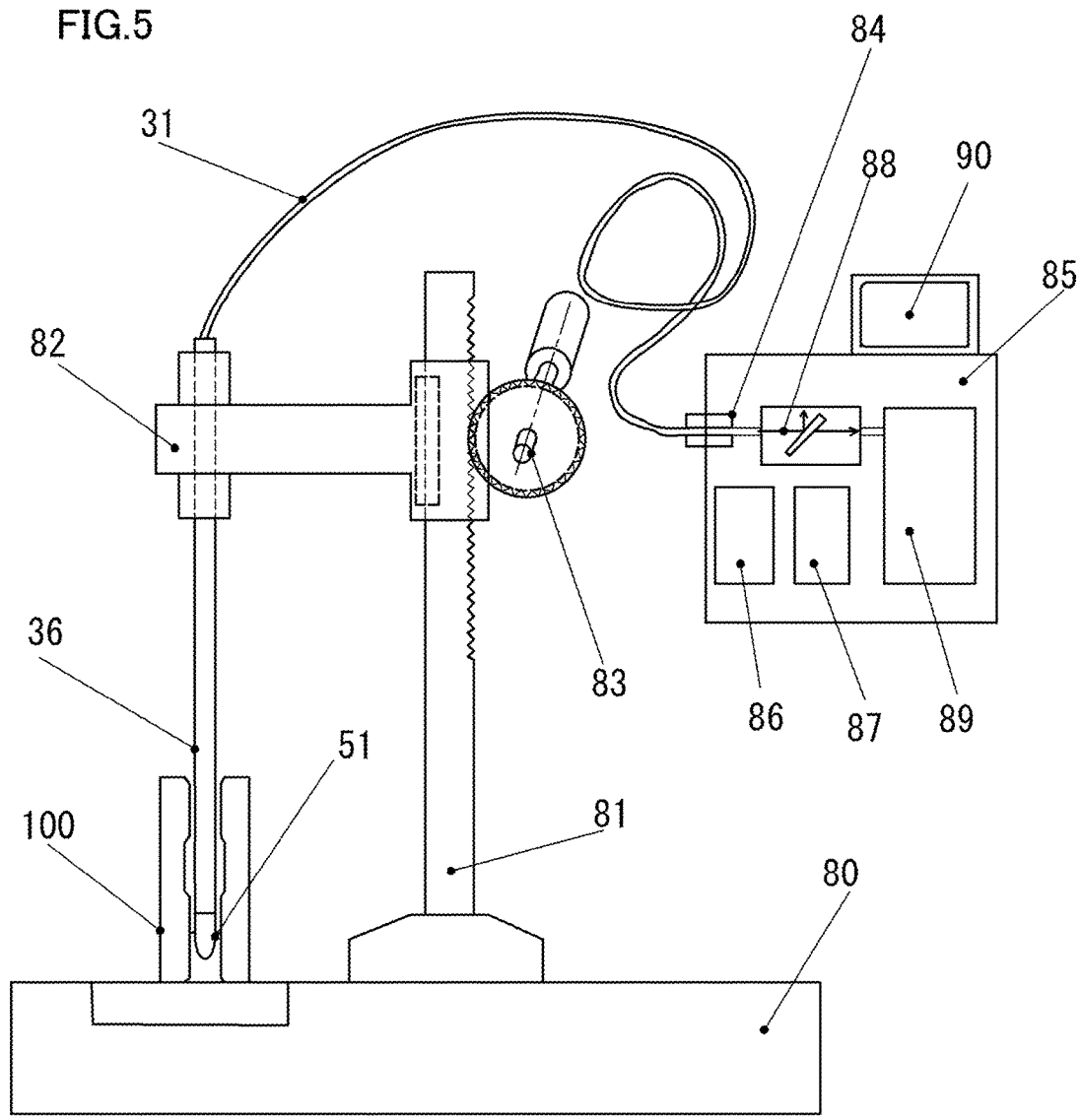
FIG. 5 illustrates a configuration of an optical inner-surface measurement device according to an embodiment of the present disclosure.
Figure 6:
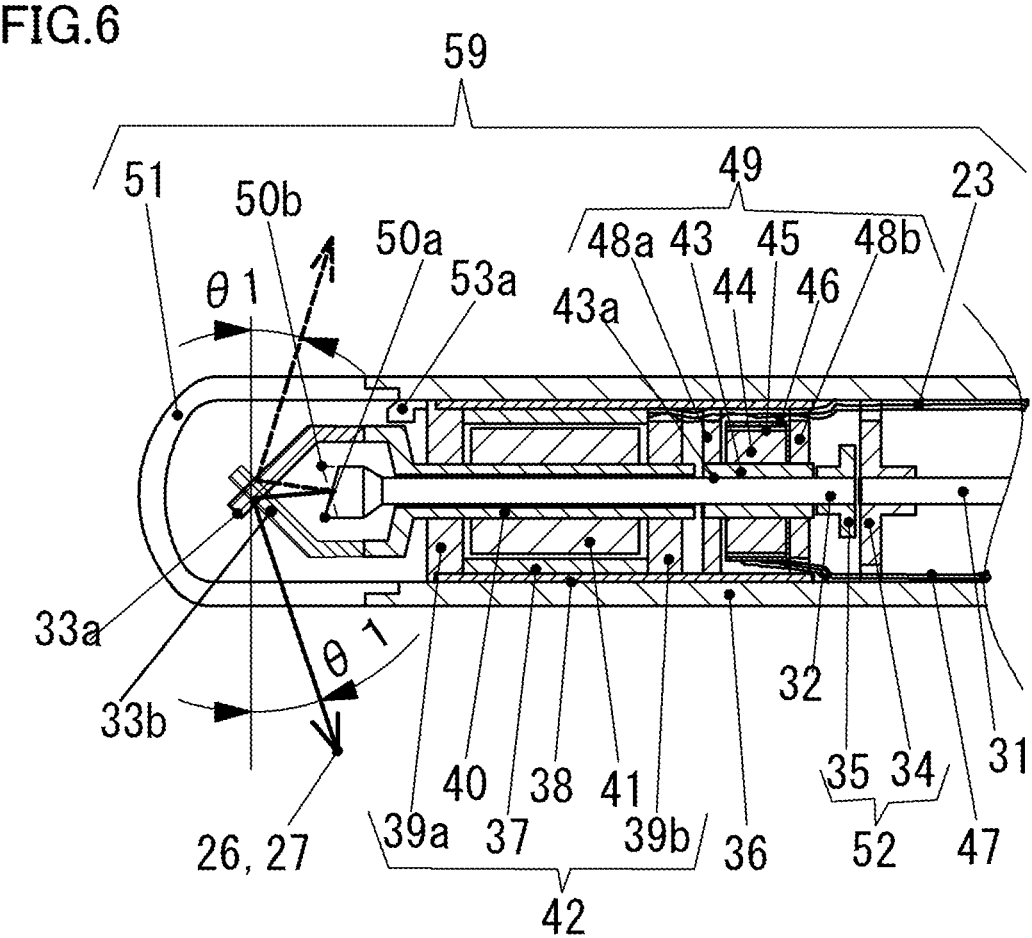
FIG. 6 is a cross-sectional view of a forward-end of an optical probe of the optical inner-surface measurement device.

FIG. 5 illustrates a configuration of the present optical inner-surface measurement device. FIG. 6 illustrates a configuration of an optical probe 59 of the present optical inner-surface measurement device.

The present optical inner-surface measurement device includes a base 80, a stand 81 fixed to the base 80, a main body 85 of the measurement device, a motor 83 for a slider, a slider 82, an optical probe 59, and a stationary-side optical fiber 31. The motor 83 for the slider causes the slider 82 and a tube 36 (optical probe 59) to move up and down together. An inspection object 100 is set on the base 80. The inspection object 100 has a hole (for example, a deep hole having a certain depth). The tube 36 (optical probe 59) ingresses into and egresses from the deep hole of the inspection object 100.

The main body 85 of the measurement device includes a connection part 84, a first motor driver circuit 86, a second motor driver circuit 87, an optical interference analyzer 88, a computer 89, and a monitor 90.

Light beam entering the stationary-side optical fiber 31 is transmitted through the tube 36, so as to be emitted to a surface (inner peripheral surface) of the deep hole of the inspection object 100. Reflected light from the inner peripheral surface of the inspection object 100 is transmitted through the tube 36, the stationary-side optical fiber 31, and the connection part 84 of the main body 85 of the measurement device, and then enters the optical interference analyzer 88.

Based on the reflected light from the inspection object 100, the optical interference analyzer 88 generates optical interference data. The optical interference data is data (interference signal) at a point in which the reflected light from the inspection object 100 and reference light interfere with each other so as to strengthen each other. The optical interference analyzer 88 includes an arithmetic unit, and generates (calculates) original waveform data based on the optical interference data and the number(s) of revolutions (and a rotational position(s)) of a first motor 42 and/or a second motor 49 (described later).

The computer 89 analyzes the original waveform data outputted from the optical interference analyzer 88, and displays, on the monitor 90, an image indicative of the result of the analysis. Furthermore, the computer 89 corrects the original waveform data using other data for a correction, so as to generate desired data (corrected data).

The present optical inner-surface measurement device has a plurality of functions (for example, six functions) as below.
(1) A function of displaying a three-dimensional shape of the inner peripheral surface of the inspection object 100 and a function (appearance inspection function) of inspecting an appearance of the inner peripheral surface of the inspection object 100, for example, the presence or absence of a burr and/or a flaw thereon.
(2) For a case where a surface film (e.g., a resin) is applied onto the inner peripheral surface, a function of measuring a thickness of the surface film, and a function of inspecting the presence or absence of a defect such as a pinhole and a projection.
(3) A surface roughness measuring function.
(4) A diameter measuring function.
(5) A roundness measuring function.
(6) A function (cylindricality measuring function) of measuring a cylindricality obtained by collecting pieces of roundness measured data continuously along a longitudinal direction and displaying the collected pieces of roundness measured data three-dimensionally.

As shown in FIG. 6, the optical probe 59 includes an electric wire 23, a rotation-side optical fiber 32, first optical-path converting elements 33a and 33b, the tube 36, the first motor 42, a vibrator 44, a piezoelectric element 45, electrodes 46, a second motor 49, an electric wire 47, second optical-path converting elements 50a and 50b, a light-transmitting member 51, a rotational optical connector 52, and a run out sensor 53a.

Hereinafter, the first optical-path converting elements 33a and 33b may be comprehensively referred to as a first optical-path converting element 33, and the second optical-path converting elements 50a and 50b may be comprehensively referred to as a second optical-path converting element 50.

The stationary-side optical fiber 31, through which a light beam is guided from a rear-end to a forward-end of the optical probe 59, is inserted into the tube 36, which has an adequately long length. The rotational optical connector 52 includes an optical-fiber fixture 34, by which the stationary-side optical fiber 31 is fixed to the tube 36.

The rotation-side optical fiber 32 is rotatably disposed so as to be adjacent to a forward-end of the stationary-side optical fiber 31. The first motor 42 is attached in a forward-end of the rotation-side optical fiber 32. The first optical-path converting elements (first optical-path convertors) 33a and 33b are, for example, substantially flat mirrors (rotational mirrors). The first optical-path converting elements 33a and 33b are attached in the forward-end of the rotation-side optical fiber 32 such that the first optical-path converting elements 33a and 33b are rotatable by the first motor 42 independently of the rotation-side optical fiber 32. The first optical-path converting elements 33a and 33b are configured to be rotated so as to emit a light beam in an entire circumferential direction.

The rotation-side optical fiber 32 and the stationary-side optical fiber 31 face each other by a very short distance of approximately 5 micrometers. The rotational optical connector (fixture) 52 optically connects the rotation-side optical fiber 32 with the stationary-side optical fiber 31. The rotational optical connector 52 includes a light-shielding plate 35, which is rotatable, and an optical-fiber fixture 34. A transmittance between the rotation-side optical fiber 32 and the stationary-side optical fiber 31 is maintained at a high level. This arrangement allows the rotation-side optical fiber 32 and the stationary-side optical fiber 31 to be optically connected with each other almost without loss.

The second optical-path converting element (second optical-path convertor) 50 is attached in the forward-end of the rotation-side optical fiber 32. The second optical-path converting element 50 collects a light beam that has been transmitted thereto through the stationary-side optical fiber 31 and the rotational optical connector 52. Then, the second optical-path converting element 50 emits the light beam toward the first optical-path converting elements 33a and 33b with a small angle in a forward-end direction while being rotated.

The first motor 42 includes a motor case 38, a motor coil 37 and first bearings 39b and 39a fixed to the motor case 38, a first hollow rotational shaft (rotational shaft) 40, which is hollow and is configured to be rotated, and a rotor magnet 41 attached to the first hollow rotational shaft 40. To the motor coil 37, voltage is applied from the electric wire 23. At least part of the forward-end of the rotation-side optical fiber 32 is inserted into a hollow hole of the first hollow rotational shaft 40 such that the rotation-side optical fiber 32 is rotatable relative to the first hollow rotational shaft 40. To the first hollow rotational shaft 40, the first optical-path converting element 33 is attached such that the first optical-path converting element 33 is rotatable integrally rotate the first optical-path converting element 33.

As well as the first motor 42, the second motor 49 includes a motor case, the vibrator 44, a second hollow rotational shaft (rotational shaft) 43, and second bearings 48a and 48b. The second bearings 48a and 48b are attached to the motor case 38, and support the second hollow rotational shaft 43 such that the second hollow rotational shaft 43 is rotatable. At least part of a rear-end of the rotation-side optical fiber 32 is fixed to a hollow hole of the second hollow rotational shaft 43. Accordingly, the second motor 49 rotates the rotation-side optical fiber 32 and the second optical-path converting element 50.

On an outer circumference of the vibrator 44, an element (an electrostrictive element or a piezoelectric element) 45 is attached. The element 45 includes the electrodes 46 formed therein. The electrodes 46 are connected to the electric wire 47, and thus voltage is applied to the electrodes 46.

The first motor 42 shown in FIG. 6 is rotationally driven by electric power supplied from the first motor driver circuit 86 shown in FIG. 5. The second motor 49 is rotationally driven by voltage applied by the second motor driver circuit 87.

The light-transmitting member 51, through which a light beam is transmittable, is attached to the tube 36 in the vicinity of an outer circumference of the first optical-path converting element 33, to which the light beam is emitted. As necessary, an inner peripheral surface or an outer peripheral surface of the light-transmitting member 51 is provided with a coating or the like for reducing surface-reflection and enhancing a transmittance of the light beam.

The first optical-path converting element 33 includes a mirror or a prism that is rotatable. The first optical-path converting element 33 has a high reflection efficiency. With this arrangement, it is possible to reduce optical loss, thereby making it possible to perform the accuracy measurement with a high accuracy.

The second optical-path converting element 50 includes, for example, a prism having a tip with an inclined, substantially-flat surface. The second optical-path converting element 50 has a high performance in collection of a light beam. With this arrangement, it is possible to reduce optical loss, thereby making it possible to perform the accuracy measurement with a high accuracy. Instead of the prism, the second optical-path converting element 50 may include a small condensing lens. Alternatively, an optical path can be formed by using the condensing lens and the prism in combination.

Next, the following specifically describes characteristic effects of the present optical inner-surface measurement device including the above-described optical imaging probe (optical probe 59) of a three-dimensional scanning type shown in FIG. 6.

In the configuration shown in FIGS. 5 and 6, a light beam such as a near-infrared light beam or a laser beam emitted from a light source in the main body 85 of the measurement device travels through the stationary-side optical fiber 31, which is included inside the tube 36.

Figure 8:
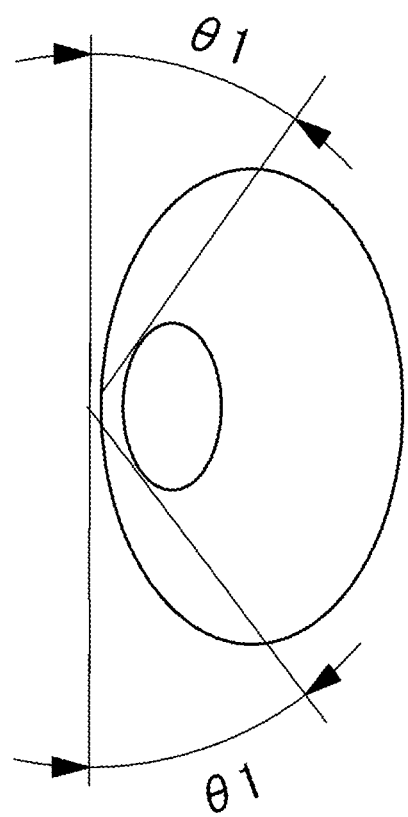
FIG. 8 is an explanatory view illustrating a scanning angle of the optical probe.

First, a rotational state (motor rotational state) of the first motor 42 and the second motor 49 is set so that the number of revolutions of the first motor 42 and the number of revolutions of the second motor 49 are substantially equal to each other. Specifically, due to electric power supplied from the electric wire 23 shown in FIG. 6, the first motor 42 and the second motor 49 are rotated at an identical number of revolutions within a range from approximately 1800 rpm to approximately 20000 rpm. A light beam guided through the stationary-side optical fiber 31 is transmitted through the rotational optical connector 52 and the rotation-side optical fiber 32, and is then emitted from the second optical-path converting element 50a. The light beam thus emitted is reflected by the substantially-flat surface of the first optical-path converting element 33a. This causes a direction of the light beam to be changed to a direction at a certain angle (an angle θ1 in FIG. 6) with respect to the original direction. Furthermore, the light beam is transmitted through the light-transmitting member 51, and is rotationally emitted toward the inner peripheral surface of the inspection object 100. A range in which the light beam is emitted in this case is an umbrella-shaped range corresponding to the angle θ1, as shown in FIG. 8.

The light beam is reflected by the inner peripheral surface of the inspection object 100. The light beam thus reflected is transmitted through the optical path identical to the above but in an opposite direction. Namely, the reflected light beam travels through the light-transmitting member 51, the first optical-path converting element 33a, the second optical-path converting element 50a, the rotation-side optical fiber 32, the rotational optical connector 52, and the stationary-side optical fiber 31 in this order, so as to be guided to the optical interference analyzer 88.

Figure 7:
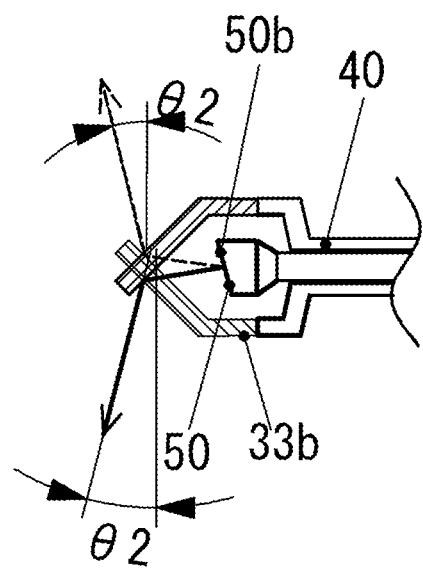
FIG. 7 is an explanatory view illustrating an optical-path converting element (rotational mirror) of the optical probe.
Figure 9:
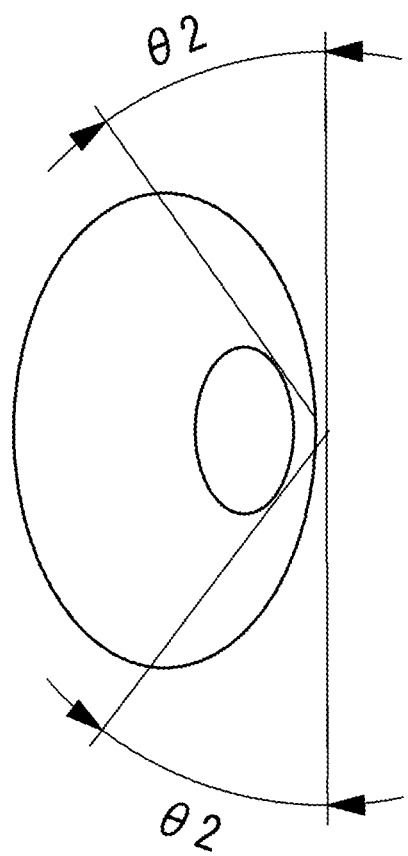
FIG. 9 is an explanatory view illustrating a scanning angle of the optical probe.

Next, the motor rotational state is changed such that the number of revolutions of the first motor 42 and the number of revolutions of the second motor 49 are slightly different from each other. For example, the number of revolutions of the first motor 42 is set at 3600 rpm constantly, whereas the number of revolutions of the second motor 49 is set at 3570 rpm constantly. In this state, as shown in FIG. 7, a phase of a rotational angle of the first optical-path converting element 33 and a phase of a rotational angle of the second optical-path converting element 50 gradually change. When a difference (rotational phase difference) between the phase of the rotational angle of the first optical-path converting element 33 and the phase of the rotational angle of the second optical-path converting element 50 reaches 180 degrees, the light beam emitted from the second optical-path converting element 50a is reflected by the first optical-path converting element 33b that is rotating. This changes a travel path of the light beam by a certain angle. A range in which the light beam is emitted in this case is changed to an umbrella-shaped range corresponding to an angle θ2, as shown in FIG. 9. Namely, in this state, the range in which the light beam is emitted has been changed to a range having inclination as those shown in FIG. 9.

The rotational phase difference changes according to a difference (namely, 30 revolutions per minute) between the number of revolutions of the first motor 42 (3600 rpm) and the number of revolutions of the second motor 49 (3570 rpm). Thus, the rotational phase difference of 360 degrees occurs every two minutes.

Figure 10:
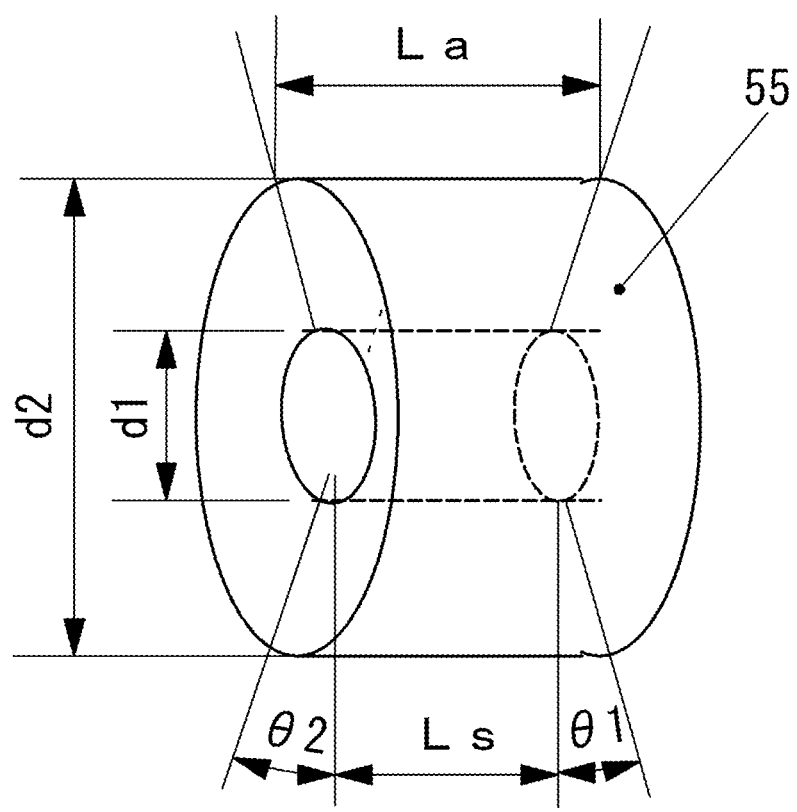
FIG. 10 is an explanatory view illustrating a three-dimensional scanning range of the optical probe.

Between the first optical-path converting element 33 and the second optical-path converting element 50, the rotational phase difference of 360 degrees (one revolution) occurs every two minutes continuously and slowly. Due to this movement, the direction in which the light beam is emitted is changed successively within a range from θ1 to θ2, as shown in FIG. 10. The range in which the light beam is emitted is a range of θ1+θ2. Within this range, the light beam is emitted three-dimensionally and repeatedly. Within the range in which the light beam is emitted (i.e., a scanning range), the signal wire and the electric wires 23 and 47 do not exist. This makes it possible to yield clear three-dimensional image data with less missing.

Thanks to the effects of the first optical-path converting element 33 and the second optical-path converting element 50, the light beam is emitted three-dimensionally in an entire circumferential direction and a longitudinal axial direction of the deep hole as shown in FIG. 10, even without causing the tube 36 to slide along the longitudinal axial direction. Thus, it is possible to perform three-dimensional scanning in a state where the motor 83 for the slider shown in FIG. 5 is stopped and thus a mechanical vibration is suppressed.

In FIG. 6, the run out sensor 53a detects a radial run out (an amount of rotational run out) of the first optical-path converting element 33 or the first hollow rotational shaft 40. Based on the amount of rotational run out, the computer 89 corrects original waveform data obtained by the optical interference analyzer 88.

As another displacement detector (displacement detecting unit) for measuring an amount of run out of the rotational shaft (first hollow rotational shaft 40) of the first motor 42, a detector as below may be employed. The alternative displacement detector detects, as an amount of rotational run out, a difference between pre-stored reference data of the shape of the inner peripheral surface or the outer peripheral surface of the tube 36 or the light-transmitting member 51, which is provided integrally with the tube 36, and measured data (original waveform data regarding the inner peripheral surface or the outer peripheral surface) of the inner peripheral surface or the outer peripheral surface of the tube 36 or the light-transmitting member 51, the measured data being obtained while the first motor 42 is rotating. The computer 89 similarly corrects the original waveform data based on the detection result, so as to yield a correct numerical value.

The following sequentially explains six measurement methods of the above-described present optical inner-surface measurement device and operations therefor.

In the below-described six measurements, a forward-end of the optical probe 59 is inserted into the deep hole of the inspection object 100, and a light beam that has been guided through the rotation-side optical fiber 32 is emitted by the two optical-path converting elements 33 and 50 three-dimensionally in a circumferential direction and an axial direction of the deep hole (see FIG. 10). The optical interference analyzer 88 obtains reflected light resulting from reflection of the light beam emitted from the two optical-path converting elements 33 and 50 in the entire circumferential direction, and performs a predetermined calculation, so as to yield original waveform data.

Figure 11:
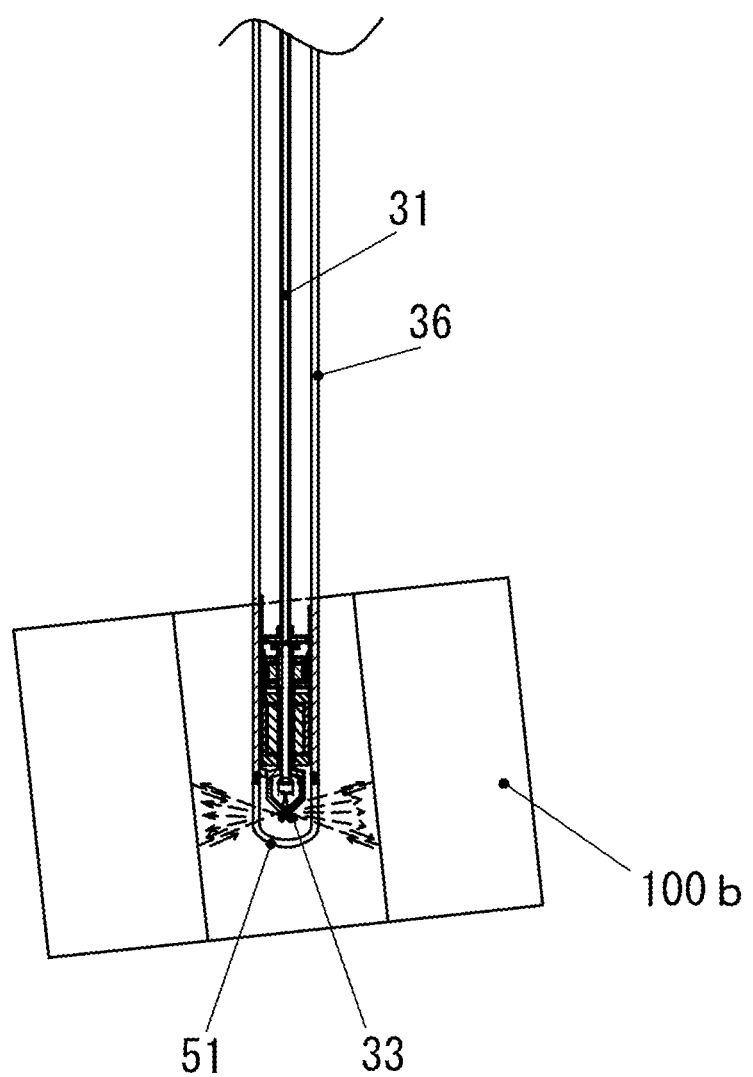
FIG. 11 is an explanatory view illustrating how the optical inner-surface measurement device operates in a state where the measurement object is inclined.
Figure 12:
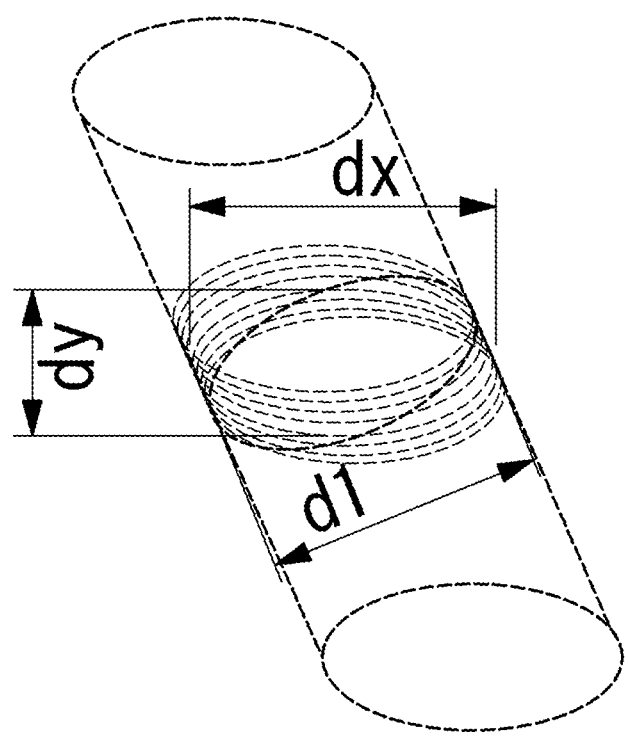
FIG. 12 is an explanatory view illustrating a method for correcting a roundness in the state where the measurement object is inclined.

(1) Displaying the three-dimensional shape and the method for inspecting the appearance such as the presence or absence of a flaw The optical interference analyzer 88 obtains reflected light from the inner peripheral surface of the inspection object 100*b* shown in FIG. 11, and yields optical interference data and original waveform data. The computer 89 performs a calculation with use of the original waveform data, so as to yield data indicative of a shape of the inner peripheral surface (for example, data indicative of a three-dimensional cylindrical shape). Furthermore, the computer 89 displays, on the monitor 90, an image of the shape of the inner peripheral surface.

For the appearance inspection, the motor 83 for the slider causes the optical probe 59 to slide in its axial direction as necessary, and reflected light is obtained three-dimensionally. Consequently, it is possible to display a three-dimensional image on the monitor 90. For the appearance inspection, a measurement accuracy of approximately 5 micrometers is necessary. Meanwhile, for a measurement of other geometric accuracy, a high accuracy of 0.02 micrometers is necessary. As compared to this, the measurement accuracy for the appearance inspection has an adequate tolerance. Thus, even if a vibration occurs in the sliding portion, it is possible to ignore an effect of the vibration.

Data of a measurement object that is free from a burr or a flaw may be memorized as reference data in advance. In this case, by comparing calculated data of a state of a surface (inner peripheral surface) of the inspection object 100 to the reference data, it is possible to find a product having a poor appearance.

(2) Next, the following describes the case where a surface film coating (e.g., a resin) is applied onto the inner peripheral surface of the inspection object 100. In this case, near-infrared light or laser light is semi-transmitted through the resin. Based on original waveform data obtained in a similar manner to that in (1), the computer 89 yields a three-dimensional image that includes an image of the film and has a high resolution. Thus, the computer 89 is able to measure a thickness of the surface layer of the inner peripheral surface of the inspection object 100 and to find a defect such as a pinhole and/or a projection thereon.

Figure 14:
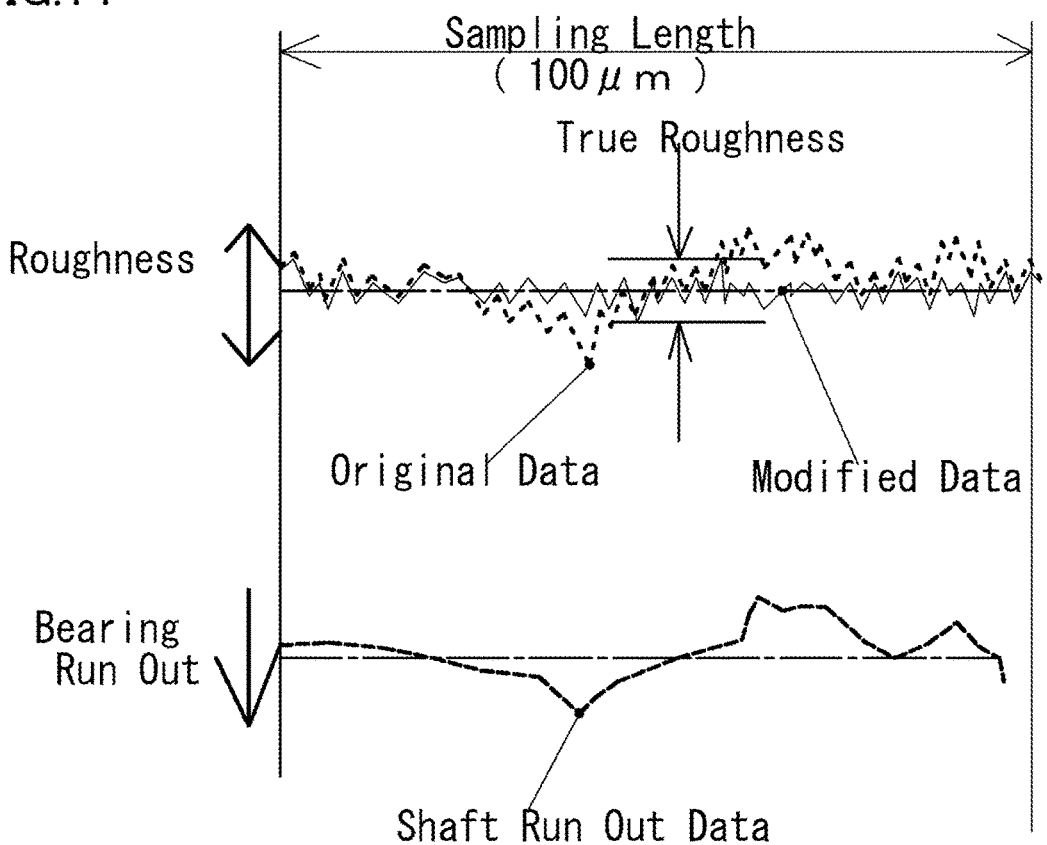
FIG. 14 is an explanatory view illustrating a method of how the optical inner-surface measurement device detects a rotational vibration and performs a correction therefor.

(3) The following describes the method for measuring a surface roughness. The computer 89 collects original waveform data of the inner peripheral surface of the inspection object 100 within a range of a sampling length (for example, a range of 100 micrometers), the original waveform data having been given by the optical interference analyzer 88. At the same time, the computer 89 collects shaft run out waveform data (run out sensor data) which is detected by a run out detector (a run out detecting unit; the run out sensor 53*a* shown in FIG. 6) and which corresponds to the radial run out of the first hollow rotational shaft 40. FIG. 14 shows one piece of original waveform data (Original Data) and one piece of shaft run out waveform data (Shaft Run Out Data). In FIG. 14, a horizontal axis indicates time.

As shown in FIG. 14, the computer 89 can yield mechanical-vibration corrected data (Modified Data; a waveform indicated by a thin solid line shown in an upper part of FIG. 14) by subtracting the shaft run out waveform data from the original waveform data. Namely, a width (a difference between a maximum value and a minimum value) of the mechanical-vibration corrected data is a true maximum surface-roughness value. In this manner, the computer 89 corrects the original waveform data by use of the radial run out data (shaft run out waveform data) of the first hollow rotational shaft 40. Thus, it is possible to measure the surface roughness with a high accuracy of, e.g., 0.01 micrometers.

(4) The following describes the method for measuring a diameter. The computer 89 performs polar coordinate transformation on the original waveform data shown in FIG. 14, so as to generate circular original waveform data. Furthermore, the computer 89 yields data indicative of a three-dimensional cylindrical shape as those shown in FIG. 12, by use of plural pieces of circular original waveform data. Moreover, based on plural pieces of original waveform data shown in FIG. 12, the computer 89 calculates an angle of inclination of the inspection object 100 (data indicative of an amount of inclination of the inspection object). Based on the result of the calculation, the computer 89 performs an angle correction on the original waveform data and the shaft run out waveform data.

Figure 15:
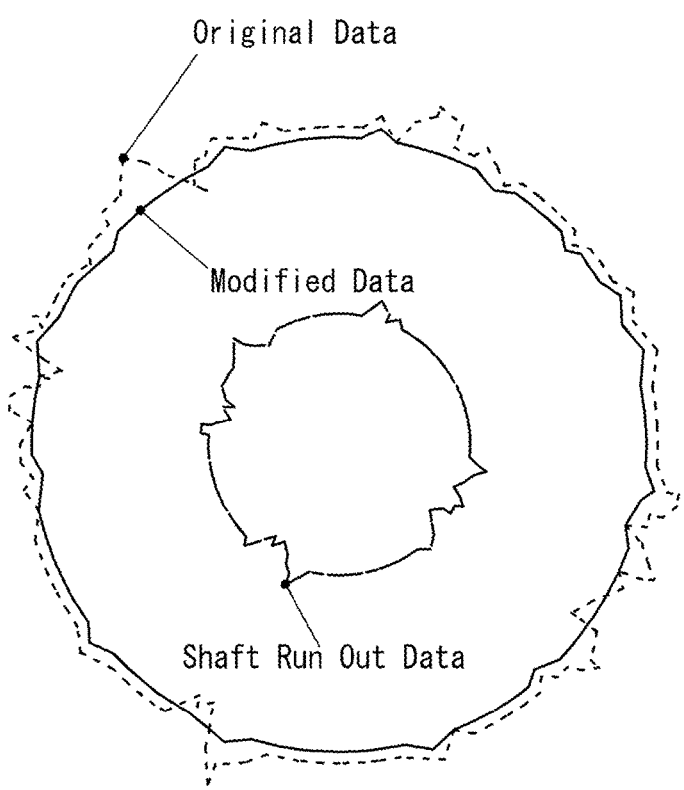
FIG. 15 is an explanatory view illustrating the method of how the optical inner-surface measurement device detects the rotational vibration and performs a correction therefor.

Original waveform data (Original Data) indicated by a dotted line and located in an outer side in FIG. 15 was obtained by performing polar coordinate transformation on the original waveform data shown in FIG. 14 and thereafter performing the angle correction thereon. This original waveform data corresponds to the shape of the inner peripheral surface of the inspection object 100. Waveform data (Shaft Run Out Data) indicated by a thick solid line and located in an inner side in FIG. 15 was obtained by correcting the angle in the shaft run out waveform data obtained by the run out detector (the run out sensor 53*a* in FIG. 6).

The computer 89 yields the mechanical-vibration corrected data, which is indicated by a thin solid line and located in the outer side in FIG. 15, by subtracting the shaft run out waveform data from the original waveform data. Furthermore, from the mechanical-vibration corrected data (Modified Data), the computer 89 yields a necessary inner diameter. Note that an actual measurement is performed as follows. Before the measurement, the present optical inner-surface measurement device is calibrated by use of a ring gauge having a guaranteed inner diameter accuracy. The measurement is performed by comparison with the guaranteed ring gauge, so that a value of a diameter is yielded and displayed.

(5) The following describes the method for measuring a roundness. In a similar manner to that in (4), the computer 89 performs an angle correction on the original waveform data and the shaft run out waveform data based on the result of the calculation of the angle of the inclination of the inspection object 100. Furthermore, as shown in FIG. 15, the computer 89 displays, on the monitor 90, the original waveform data (Original Data) and the shaft run out waveform data (Shaft Run Out Data) each corrected for the angle of the inclination and mechanical-vibration corrected data (Modified Data), which is a difference between the original waveform data (Original Data) and the shaft run out waveform data (Shaft Run Out Data). Moreover, the computer 89 calculates an inscribed circle and a circumscribed circle from the mechanical-vibration corrected data shown in FIG. 15. A radial difference between the two circles can be defined as the roundness. This value (radial difference) is displayed on the monitor 90.

According to this arrangement, reflected light is guided from the inner peripheral surface of the inspection object 100 to the main body 85 of the measurement device through the optical fiber 32. The optical interference analyzer 88 and the computer 89 perform a calculation based on the reflected light, so as to yield data indicative of the shape of the inner peripheral surface of the inspection object 100. In this manner, this measurement is performed without causing the optical fibers 31 and 32 to move in the axial direction. Consequently, this measurement is performed without occurrence of a sliding vibration of the tube 36 or a vibration of the motor 83 for the slider. Note that the vibration caused by the sliding is difficult to be detected and corrected. Therefore, the measurement is preferably performed without a sliding operation.

Furthermore, the run out sensor 53a detects the angle of the inclination of the inspection object 100 and mechanical vibrations of the first motor 42 and the second motor 49 (a radial run out of the first optical-path converting element 33 or the first hollow rotational shaft 40). Based on the result of the detection (rotational vibration data), the computer 89 corrects the original waveform data and/or the like. This makes it possible to correctly measure the roundness of the inner peripheral surface.

Figure 13:
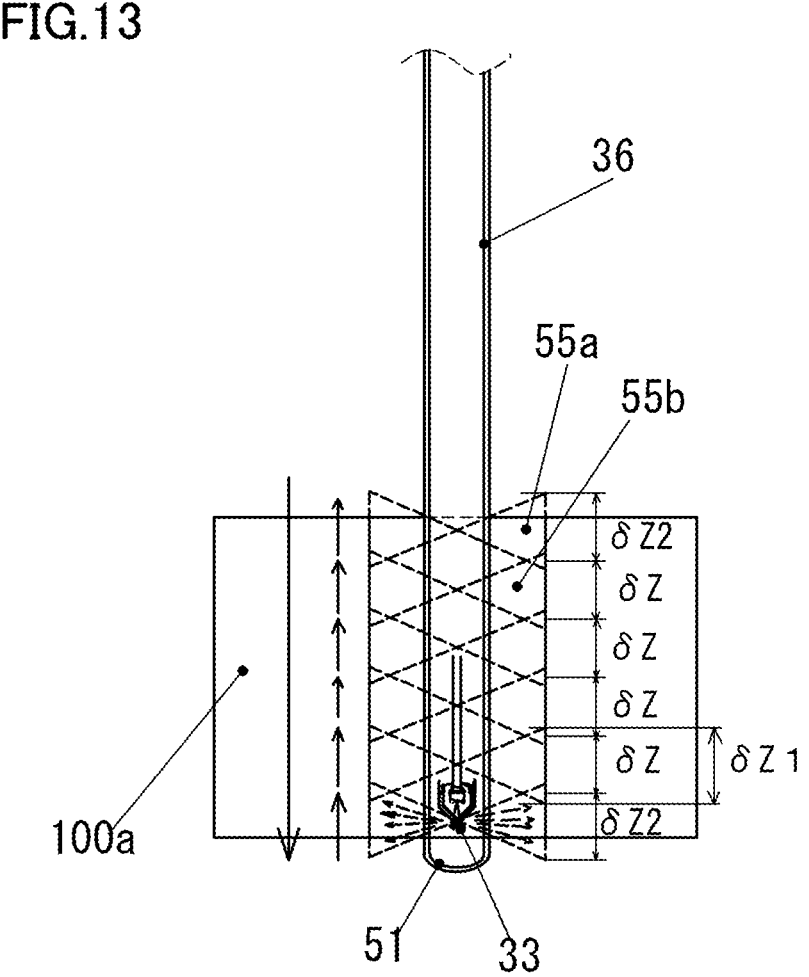
FIG. 13 is an explanatory view illustrating how the optical inner-surface measurement device measures a cylindricality.

(6) The following describes the method for measuring a cylindricality. During this measurement, the motor 83 for the slider shown in FIG. 5 is stopped, so that a vibration is not caused by the motor. As shown in FIG. 13, the computer 89 obtains plural pieces of original waveform data and plural pieces of shaft run out waveform data within a range of δZ1 shown in FIG. 13. During this, in a similar manner to that in (4), the computer 89 performs an angle correction on the plural pieces of original waveform data and the plural pieces of shaft run out waveform data based on the calculation result of the angle of the inclination of the inspection object 100a. The computer 89 then obtains plural pieces of mechanical-vibration corrected data, which are differences between the plural pieces of original waveform data and the plural pieces of shaft run out waveform data. Together with the slider 82 shown in FIG. 5, the optical probe 59 is advanced into the inspection object 100a intermittently by a distance δZ at each time.

The computer 89 connects, one to another, the pieces of the mechanical-vibration corrected data obtained at every distance δZ, so as to yield the mechanical-vibration corrected data corresponding to the whole cylinder. The computer 89 calculates, as a cylindricality, a radial difference between an inscribed cylinder and a circumscribed cylinder in the mechanical-vibration corrected data (a three-dimensional image of the cylinder) corresponding to the whole cylinder. The computer 89 then displays the result of the calculation. Also in this measurement, the data is obtained while the motor 83 for the slider is not rotated. Thus, a vibration or a noise hardly occurs. Therefore, it is possible to perform the measurement with a high accuracy.

Figure 16:
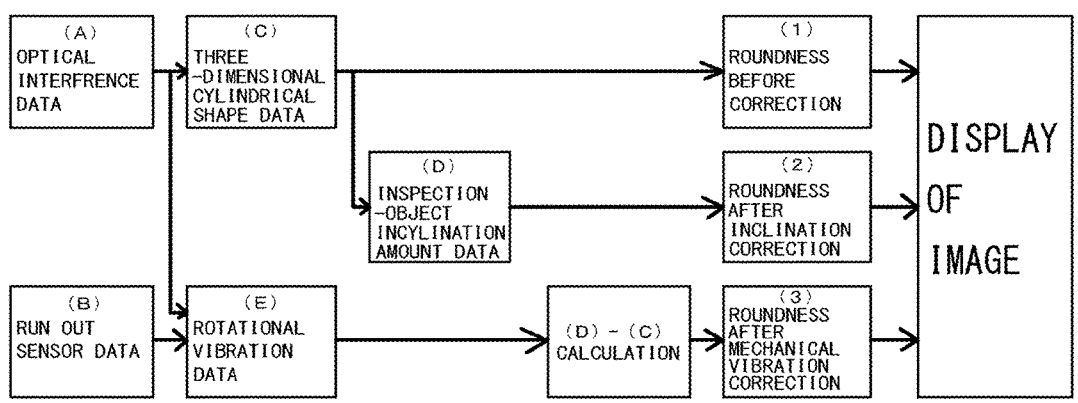
FIG. 16 is a flow diagram illustrating how the optical inner-surface measurement device performs a calculation for a correction.

FIG. 16 is a flow diagram illustrating how the optical inner-surface measurement device performs a calculation for a correction. As described so far, based on data indicative of an amount of inclination of the inspection object 100 (D) shown in FIG. 16, it is possible to yield a corrected roundness (2). By detecting rotational vibration data (E), it is possible to yield measurement values of a roundness (3) corrected for a mechanical vibration, a surface roughness, and a cylindricality.

Note that the data indicative of the three-dimensional cylindrical-shape shown in FIG. 16 can be obtained in the following manner. Based on optical interference data, the number(s) of revolutions of the first motor 42 and/or the second motor 49, and information of a rotational position(s) of the first motor 42 and/or the second motor 49, the optical interference analyzer 88 yields data indicative of a shape as those shown in FIG. 14. The optical interference analyzer 88 converts the data indicative of the shape into circular original waveform data as those shown in FIG. 15. The computer 89 overlays plural pieces of circular original waveform data on one another, so as to yield data indicative of a three-dimensional cylindrical shape as those illustrated in FIG. 12.

The correction for the angle of inclination may be or may not be performed in the appearance inspection and the inspection of the defect of a pinhole or a projection. Some of the measurements (1) to (6) may be performed simultaneously.

The displacement detector for measuring an amount of run out of the first hollow rotational shaft 40 of the first motor 42 may be at least one run out sensor 53a, which faces an outer peripheral surface of the first hollow rotational shaft 40 (first optical-path converting element 33), as shown in FIG. 6. However, there are other examples of the displacement detector. One example of the displacement detector for measuring the amount of run out of the first hollow rotational shaft 40 of the first motor 42 may be a detector as below. That is, the displacement detector is detectable, as the amount of run out, a difference between pre-stored reference data of the shape of the inner peripheral surface of the tube 36 and original waveform data of the inner peripheral surface of the light-transmitting member 51 or the tube 36 and is obtained while the first motor 42 is rotating. In this case, the data (Shaft Run Out Data) indicated by the thick solid line and located in the inner side in FIG. 15 is the data indicative of the amount of run out (shaft run out waveform data) that is calculated based on the difference between the reference data of the shape of the inner peripheral surface of the tube 36 and the original waveform data obtained while the first motor 42 is rotating.

Also with this arrangement and this detection method, it is possible to remove, from the collected original waveform data, effects of a distortion and a vibration in an image given to the data indicative of the shape of the inner peripheral surface of the inspection object 100. This makes it possible to correctly and accurately measure accuracies of the inner diameter and the inner peripheral surface. In this case, the light-transmitting member 51 is made of glass or a transparent resin. Furthermore, as necessary, a metal coating having a thickness of some nanometers and transparency may be applied onto the inner peripheral surface of the light-transmitting member 51. Consequently, it is possible to more reliably detect a contour of a waveform collected from the inner peripheral surface.

Note that the tube 36 has a diameter of, for example, approximately 2 millimeters. The stationary-side optical fiber 31, which internally penetrates through the tube 36, is a glass fiber that is bendable, for example. The stationary-side optical fiber 31 has a diameter of, for example, approximately 0.1 millimeters to 0.4 millimeters.

The first optical-path converting element 33 shown in FIG. 6 includes a mirror or a prism having a flat reflection surface. In order to enhance the reflectivity, the surface of the first optical-path converting element 33 may have been polished and accordingly have accuracies of a surface roughness and a flatness that are equal to or higher than those of a general optical element.

The first hollow rotational shaft 40 shown in FIG. 6 is made of, for example, metal or ceramic. For example, the first hollow rotational shaft 40 is manufactured as follows. That is, a molten metal is subjected to a drawing process with a die or a ceramic before firing is subjected to extrusion with a die, so that a hollow product is obtained. The product is cured, and then the cured product is finished by, e.g., polishing.

In FIG. 6, the first hollow rotational shaft 40 has a hole having a diameter of, for example, 0.2 millimeters to 0.5 millimeters, which is adequately larger than the diameter of the stationary-side optical fiber 31. Therefore, the stationary-side optical fiber 31, which is fixed by the optical-fiber fixture 34, hardly comes in contact with the first hollow rotational shaft 40. Even if the stationary-side optical fiber 31 comes in slight contact with the first hollow rotational shaft 40, the contact is not strong enough to occur abrasion powder, and hardly changes a rotational friction torque.

One of necessary characteristics of this type of device for observing and inspecting the inner surface by three-dimensional scanning is an enhanced spatial resolution. The spatial resolution is determined by factors such as a variation in a rotational speed of the first motor 42, accuracies of run out and non-repeatable run out of the first hollow rotational shaft 40, and a processing accuracy of the first optical-path converting element 33.

Among these, for the variation in the rotational speed of the first motor 42, the present embodiment has the following arrangement. That is, the first motor 42 is included inside the forward-end of the optical probe 59. With this arrangement, the stationary-side optical fiber 31 is not rotated inside the tube 36. This reduces a possibility that, due to occurrence of a frictional force, a variation in the rotational speed occurs and accordingly a distortion and a noise are given to collected data. Thus, this arrangement stably provides a high three-dimensional spatial resolution.

For the accuracies of the run out and the non-repeatable run out of the first hollow rotational shaft 40, the present embodiment has the following arrangement. That is, run out is detected by the run out sensor 53a, and an effect of the run out is canceled. Accordingly, data of an inner diameter is measured correctly. In such an arrangement, the first motor 42, the second motor 49, and the rotational optical connector 52, which are shown in FIG. 6, are not necessarily included inside the forward-end of the tube 36. Alternatively, the first motor 42, the second motor 49, and the rotational optical connector 52 may be disposed in the tube 36 shown in FIG. 11 in a position close to the device (i.e., in an upper part of FIG. 11). In this case, the rotation-side optical fiber 32 may be configured so as to have an adequately long length.

According to the present optical inner-surface measurement device, in a state where the optical probe 59 is not being slid along the longitudinal axial direction but is stationary, the two optical-path converting elements 33 and 50 emit a light beam guided thereto through the optical fibers 31 and 32, three-dimensionally in the circumferential direction and the axial direction. With this, it is possible to calculate inclination of the inspection object 100 and to yield a roundness by performing a correction for the inclination. Furthermore, the present optical inner-surface measurement device includes the run out detector (run out sensor 53a) for detecting an amount of run out of the rotational shaft (first hollow rotational shaft 40) of the first motor 42. By correcting original waveform data with use of radial run out data (data indicative of an amount of displacement) corresponding to an amount of run out detected, it is possible to remove almost all measurement errors contained in data indicative of a shape of the inner peripheral surface of the inspection object 100, and thereby to perform a measurement with a high accuracy.

The optical inner-surface measurement device for observing and measuring the inspection object with use of the interference optical technique according to the present embodiment is applicable to an industrial diagnostic device to perform a measurement with a high accuracy and a three-dimensional observation of, e.g., a deep hole. Furthermore, such a device is expected to be employed in a medical site to numerically diagnose a size of a quite small lesion and perform a treatment for the lesion.

Note that, according to the present embodiment, the optical interference analyzer 88 includes the arithmetic unit, and calculates original waveform data based on optical interference data and the number(s) of revolutions of the first motor 42 and/or the second motor 49. Alternatively, the optical interference analyzer 88 may not include the arithmetic unit. In this case, the computer 89 generates original waveform data based on optical interference data generated by the optical interference analyzer 88.

The present disclosure may alternatively be expressed as relating to an optical inner-surface measurement device for causing an optical measurement probe to be advanced to an inner peripheral surface of a measurement object or into an inner diameter of a deep hole of the measurement object, emitting a light beam to the inner surface or a bottom surface of the deep hole, and obtaining reflected light three-dimensionally, so as to observe an internal shape of the measurement object and measure a dimension and a geometric accuracy of the measurement object.

Embodiments of the present disclosure may be first to eighth optical inner-surface measurement devices as below. The first optical inner-surface measurement device is an optical inner-surface measurement device for observing and measuring an inspection object by means of an interference optical technique, the optical inner-surface measurement device including: an optical fiber included inside a tube; at least two optical-path converters disposed in a forward-end of the optical fiber; and a motor for rotationally driving at least one of the two optical-path converters, the forward-end of the optical fiber being configured to be inserted into an inner diameter of the inspection object, the two optical-path converters being configured to emit a light beam guided thereto through the optical fiber, three-dimensionally in a circumferential direction and an axial direction.

The second optical inner-surface measurement device is the first optical inner-surface measurement device configured such that: the light beam three-dimensionally emitted by the two optical-path converters is guided to an optical interference analyzer through the optical fiber; and a computer calculates an angle of inclination of the inspection object and calculates a roundness of the inner diameter.

The third optical inner-surface measurement device is the first or second optical inner-surface measurement device configured to include a displacement detecting unit for measuring an amount of rotational run out of the optical-path converter that is rotating.

The fourth optical inner-surface measurement device is any one of the first to third optical inner-surface measurement devices configured such that the displacement detecting unit is at least one sensor disposed so as to face an outer peripheral surface of the optical-path converter that is rotating.

The fifth optical inner-surface measurement device is any one of the first to fourth optical inner-surface measurement devices configured to correct reflected light from the inspection object obtained through the optical fiber, the correction being performed based on data that is indicative of a shape of the inner peripheral surface of the inspection object and is obtained by a calculation performed by the computer, and data that is indicative of an amount of displacement and is given by the displacement detecting unit.

The sixth optical inner-surface measurement device is any one of the first to fifth optical inner-surface measurement devices configured such that the displacement detecting unit detects, as an amount of run out, a difference between reference data of a shape of an inner periphery of the tube or a light-transmitting part provided integrally with the tube and measured data of the inner peripheral surface or an outer peripheral surface of the tube, the measured data of the inner surface or the outer surface being obtained at the same time while a rotational shaft is rotating.

The seventh optical inner-surface measurement device is any one of the first to sixth optical inner-surface measurement devices configured such that: the motor is disposed in the forward-end of the optical fiber; the rotational shaft is hollow; the optical-path converter is disposed such that the optical-path converter is rotatable integrally with the rotational shaft; and the optical fiber is configured to be inserted into a hollow hole of the rotational driving shaft such that the optical fiber is rotatable relative to the rotational shaft.

The eighth optical inner-surface measurement device is any one of the first to seventh optical inner-surface measurement devices configured such that: the first motor and a second motor disposed behind the first motor are provided as the motor; a first optical-path convertor configured to be driven by the first motor and a second optical-path convertor configured to be driven by the second motor are provided as the optical-path converter; the optical fiber is constituted by a stationary-side optical fiber unrotatably fitted to the tube by a fixture in a position behind the second motor and a rotation-side optical fiber rotatable integrally with one of rotational shafts of the first motor and the second motor; the first motor and the second motor include the respective rotational shafts each being hollow; at least part of the forward-end of the rotation-side optical fiber is inserted into a hollow hole of the rotational shaft of the first motor, and at least part of a rear portion of the rotation-side optical fiber is fixed to a hollow hole of the rotational shaft of the second motor; the first optical-path convertor is disposed so as to be adjacent to a forward-end of the second optical-path convertor such that the first optical-path convertor is rotatable integrally with the rotational shaft of the first motor; and the second optical-path convertor is provided in a forward-end of the rotation-side optical fiber.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. An optical inner-surface measurement device comprising:
    an optical fiber included inside a tube, the optical fiber being configured to be inserted into a hole of an inspection object;
    at least two optical-path converting elements disposed in a forward-end of the optical fiber, the at least two optical-path converting elements emitting a light beam, guided thereto through the optical fiber, to an inner peripheral surface of the hole of the inspection object three-dimensionally in a circumferential direction and an axial direction of the hole;
    a motor for rotationally driving at least one of the at least two optical-path converting elements;
    an optical interference analyzer for receiving reflected light via the optical fiber and generating original waveform data regarding the inner peripheral surface, the reflected light being obtained by the light beam emitted three-dimensionally being reflected by the inner peripheral surface; and
    a computer for correcting the original waveform data,
    wherein the computer calculates an angle of inclination of the inspection object, and corrects the original waveform data based on a result of the calculation of the angle of the inclination.

2. The optical inner-surface measurement device according to claim 1, wherein
    the computer calculates a roundness of the inner peripheral surface by correcting the original waveform data.

3. The optical inner-surface measurement device according to claim 1, further comprising
    a displacement detector for measuring an amount of rotational run out of at least one of the at least two optical-path converting elements that is rotating, wherein
    the computer corrects the original waveform data based on the amount of rotational run out.

4. An optical inner-surface measurement device comprising:
    an optical fiber included inside a tube, the optical fiber being configured to be inserted into a hole of an inspection object;
    at least two optical-path converting elements disposed in a forward-end of the optical fiber, the at least two optical-path converting elements emitting a light beam, guided thereto through the optical fiber, to an inner peripheral surface of the hole of the inspection object three-dimensionally in a circumferential direction and an axial direction of the hole;
    a motor for rotationally driving at least one of the at least two optical-path converting elements;
    an optical interference analyzer for receiving reflected light via the optical fiber and generating original waveform data regarding the inner peripheral surface, the reflected light being obtained by the light beam emitted three-dimensionally being reflected by the inner peripheral surface;
    a displacement detector for measuring an amount of rotational run out of at least one of the at least two optical-path converting elements that is rotating, the displacement detector including at least one sensor facing an outer peripheral surface of at least one of the at least two optical-path converting elements that is rotating; and a computer for correcting the original waveform data based on the amount of rotational run out.

5. The optical inner-surface measurement device according to claim 3, wherein
the computer generates data indicative of a shape of the inner peripheral surface of the inspection object by correcting the original waveform data based on the amount of rotational run out.

6. An optical inner-surface measurement device comprising:
an optical fiber included inside a tube, the optical fiber being configured to be inserted into a hole of an inspection object;
at least two optical-path converting elements disposed in a forward-end of the optical fiber, the at least two optical-path converting elements emitting a light beam, guided thereto through the optical fiber, to an inner peripheral surface of the hole of the inspection object three-dimensionally in a circumferential direction and an axial direction of the hole;
a motor for rotationally driving at least one of the at least two optical-path converting elements;
an optical interference analyzer for receiving reflected light via the optical fiber and generating original waveform data regarding the inner peripheral surface, the reflected light being obtained by the light beam emitted three-dimensionally being reflected by the inner peripheral surface;
a displacement detector for measuring an amount of rotational run out of at least one of the at least two optical-path converting elements that is rotating, the displacement detector being configured to detect, as the amount of rotational run out, a difference between reference data of a shape of an inner peripheral surface or an outer peripheral surface of the tube or a light-transmitting member provided integrally with the tube and original waveform data regarding the inner peripheral surface or the outer peripheral surface, the original waveform data being obtained while the motor is rotating; and
a computer for correcting the original waveform data based on the amount of rotational run out.

7. The optical inner-surface measurement device according to claim 1, wherein
the optical fiber includes a rotation-side optical fiber,
the motor includes a first motor being disposed in a forward-end of the rotation-side optical fiber and including a rotational shaft that is hollow,
the at least two optical-path converting elements include a first optical-path converting element, the first optical-path converting element being provided in a forward-end of the rotational shaft such that the first optical-path converting element is rotatable integrally with the rotational shaft, and
at least part of the forward-end of the rotation-side optical fiber is inserted into a hollow hole of the rotational shaft such that the at least part of the forward-end of the rotation-side optical fiber is rotatable relative to the rotational shaft.

8. An optical inner-surface measurement device comprising:
an optical fiber included inside a tube, the optical fiber being configured to be inserted into a hole of an inspection object;
at least two optical-path converting elements disposed in a forward-end of the optical fiber, the at least two optical-path converting elements emitting a light beam, guided thereto through the optical fiber, to an inner peripheral surface of the hole of the inspection object three-dimensionally in a circumferential direction and an axial direction of the hole; and
a motor for rotationally driving at least one of the at least two optical-path converting elements,
wherein
the optical fiber includes a rotation-side optical fiber,
the motor includes a first motor being disposed in a forward-end of the rotation-side optical fiber and including a rotational shaft that is hollow,
the at least two optical-path converting elements include a first optical-path converting element, the first optical-path converting element being provided in a forward-end of the rotational shaft such that the first optical-path converting element is rotatable integrally with the rotational shaft,
at least part of the forward-end of the rotation-side optical fiber is inserted into a hollow hole of the rotational shaft such that the at least part of the forward-end of the rotation-side optical fiber is rotatable relative to the rotational shaft,
the motor further includes a second motor disposed behind the first motor,
the optical fiber includes a stationary-side optical fiber disposed behind the second motor and optically connected to the rotation-side optical fiber via a fixture,
the second motor includes a rotational shaft that is hollow,
at least part of a rear portion of the rotation-side optical fiber is fixed to a hollow hole of the rotational shaft of the second motor, and
the at least two optical-path converting elements include a second optical-path converting element attached to the forward-end of the rotation-side optical fiber.

* * * * *